United States Patent
Nordin

(10) Patent No.: US 10,466,225 B2
(45) Date of Patent: Nov. 5, 2019

(54) METHOD AND SYSTEM FOR DETECTION OF FUEL QUALITY USING ENGINE POWER OUTPUT AND NOX EMISSION VALUES

(71) Applicant: SCANIA CV AB, Södertälje (SE)

(72) Inventor: Mikael Nordin, Järna (SE)

(73) Assignee: SCANIA CV AB (SE)

( * ) Notice: Subject to any disclaimer, the term of this patent is extended or adjusted under 35 U.S.C. 154(b) by 196 days.

(21) Appl. No.: 14/787,058

(22) PCT Filed: Apr. 25, 2014

(86) PCT No.: PCT/SE2014/050507
§ 371 (c)(1),
(2) Date: Oct. 26, 2015

(87) PCT Pub. No.: WO2014/178779
PCT Pub. Date: Nov. 6, 2014

(65) Prior Publication Data
US 2016/0069855 A1 Mar. 10, 2016

(30) Foreign Application Priority Data
Apr. 30, 2013 (SE) ........................... 1350527

(51) Int. Cl.
*G01N 33/28* (2006.01)
*F02D 41/14* (2006.01)
(Continued)

(52) U.S. Cl.
CPC ....... *G01N 33/2829* (2013.01); *F01N 13/008* (2013.01); *F02D 19/06* (2013.01);
(Continued)

(58) Field of Classification Search
CPC .......................... G01N 33/2829; G01N 33/22; F02D 41/1462; F02D 41/1461; F02D 19/06
See application file for complete search history.

(56) References Cited

U.S. PATENT DOCUMENTS

| 5,140,965 A | * | 8/1992 | Nogi | .................. F02D 41/0025 |
|---|---|---|---|---|
| | | | | 123/1 A |
| 5,179,926 A | * | 1/1993 | Ament | ................ F02D 41/0025 |
| | | | | 123/1 A |

(Continued)

FOREIGN PATENT DOCUMENTS

| DE | 102008042925 B3 | 6/2010 |
|---|---|---|
| EP | 2 581 588 A1 | 4/2013 |
| KR | 20030020116 | 3/2003 |

OTHER PUBLICATIONS

Dec. 2016: Interim Eligibility Guidance Quick Reference Sheet.*
(Continued)

*Primary Examiner* — Michele Fan
(74) *Attorney, Agent, or Firm* — Ostrolenk Faber LLP

(57) ABSTRACT

A method and a system for detecting a fuel quality in a vehicle including a first determination unit to determine a correction factor $k_{kW}$ for fuel as a quotient between an output $fo_{kW}$ required to propel a vehicle and a reference output $eng_{kW}$ which an engine in the vehicle is estimated to yield;

$$k_{kW} = \frac{fo_{kW}}{eng_{kW}};$$

Figure 1:
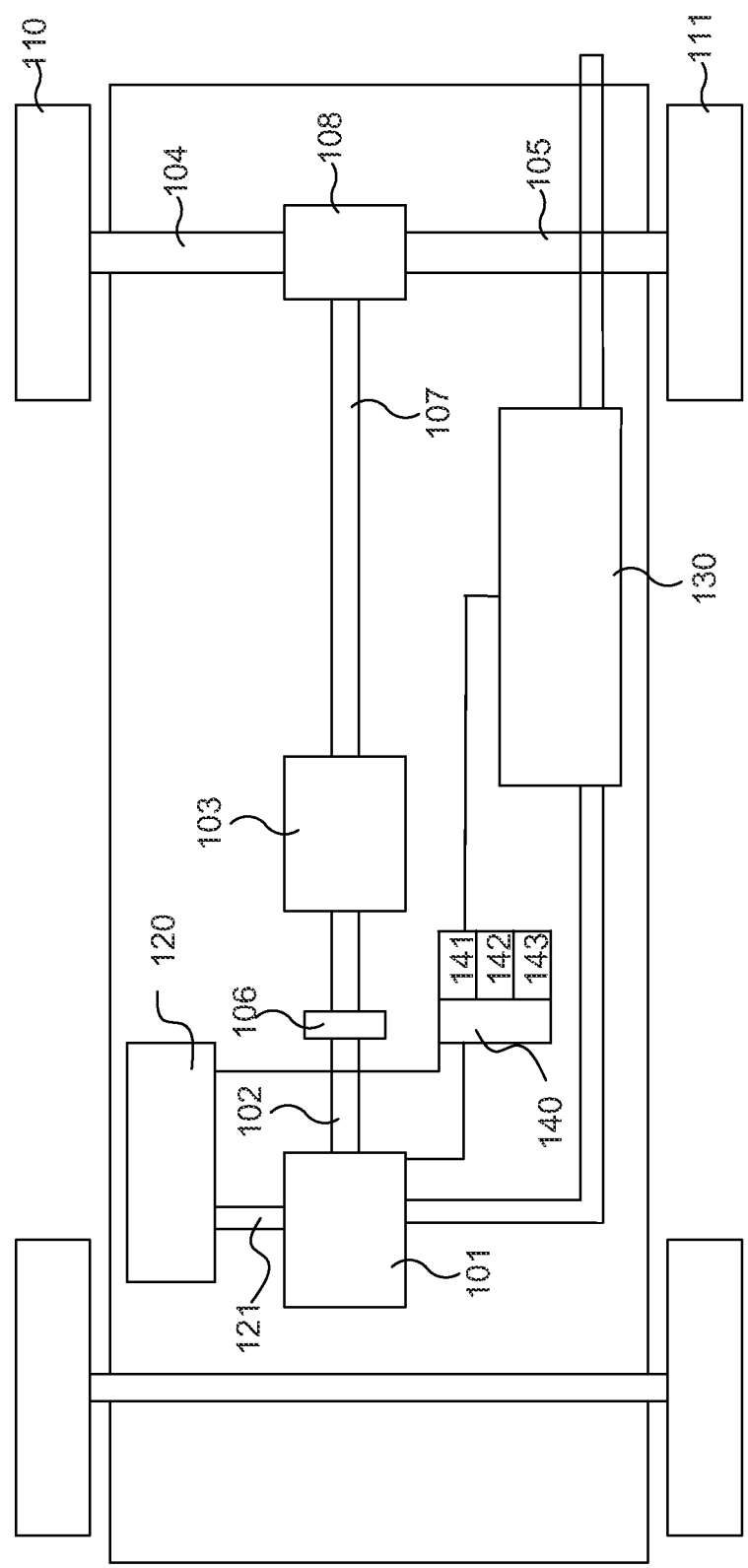

a second determination unit to determine a correction factor $k_{NOx}$ for exhaust gas emissions as a quotient between a value measured in the vehicle for nitrogen oxides $eng_{NOx}$ and a reference value for nitrogen oxides $ECU_{NOx}$;

$$k_{NOx} = \frac{eng_{NOx}}{ECU_{NOx}};$$

(Continued)

and a detection unit to detect the fuel quality based on a relation between the correction factor $k_{kW}$ for fuel and the correction factor $k_{NOx}$ for exhaust gas emissions.

23 Claims, 3 Drawing Sheets

(51) Int. Cl.
    *F02D 19/06*      (2006.01)
    *G01N 33/22*      (2006.01)
    *F01N 13/00*      (2010.01)
    *F02D 41/00*      (2006.01)

(52) U.S. Cl.
    CPC ..... *F02D 41/1461* (2013.01); *F02D 41/1462* (2013.01); *F02D 41/1497* (2013.01); *G01N 33/22* (2013.01); *F02D 41/0025* (2013.01); *F02D 2200/0612* (2013.01); *Y02T 10/36* (2013.01)

(56) References Cited

U.S. PATENT DOCUMENTS

| | | | | |
|---|---|---|---|---|
| 6,249,215 | B1* | 6/2001 | Dilz | B60R 25/043 180/287 |
| 7,191,772 | B2* | 3/2007 | Robitschko | F02D 19/081 123/299 |
| 2003/0163249 | A1* | 8/2003 | Kapolka | G08G 1/20 701/123 |
| 2005/0177300 | A1* | 8/2005 | Herdin | F02D 19/029 701/103 |
| 2005/0247504 | A1* | 11/2005 | Gleasman | B60K 17/105 180/307 |
| 2007/0204674 | A1 | 9/2007 | Takaku | |
| 2008/0096713 | A1* | 4/2008 | Beson | F16H 3/721 475/16 |
| 2010/0312423 | A1* | 12/2010 | Steinhauser | B60K 6/48 701/22 |
| 2011/0093146 | A1* | 4/2011 | Falkenstein | B60W 10/02 701/22 |
| 2011/0106399 | A1* | 5/2011 | Asano | F02D 35/02 701/102 |
| 2012/0036837 | A1* | 2/2012 | Hodgson | B01D 53/90 60/281 |
| 2014/0074379 | A1* | 3/2014 | Aoyagi | F02D 41/2454 701/104 |
| 2014/0311123 | A1* | 10/2014 | Gonze | F01N 3/103 60/274 |

OTHER PUBLICATIONS

Aug. 2017: Interim Eligibility Guidance Quick Reference Sheet (https://www.uspto.gov/patent/laws-and-regulations/examination-policy/subject-matter-eligibility).*
*Digitech Image Techs., LLC* v. *Elecs. for Imaging, Inc.*, 111 USPQ2d 1717 (Fed. Cir. 2014).*
*Electric Power Group, LLC* v. *Alstom S.A.*, (Fed. Cir. 2016).*
*Parker* v. *Flook*, 198 USPQ 193 (U.S. 1978).*
In re Grams, 12 USPQ2d 1824 (Fed. Cir. 1989).*
International Search Report dated Aug. 15, 2014 issued in corresponding International patent application No. PCT/SE2014/050507.

* cited by examiner

METHOD AND SYSTEM FOR DETECTION OF FUEL QUALITY USING ENGINE POWER OUTPUT AND NOX EMISSION VALUES

CROSS-REFERENCE TO RELATED APPLICATIONS

The present application is a 35 U.S.C. §§ 371 national phase conversion of PCT/SE2014/050507, filed Apr. 25, 2014, which claims priority of Swedish Patent Application No. 1350527-6, filed Apr. 30, 2013, the contents of which are incorporated by reference herein. The PCT International Application was published in the English language.

TECHNICAL SCOPE

The present invention relates to a method for detecting fuel quality, to a system configured to detect fuel quality and to a computer program and a computer program product which implement the method according to the invention.

BACKGROUND OF THE INVENTION

The following background description comprises a description of the background to the present invention and thus does not necessarily constitute prior art.

Modern-day combustion engines can use various kinds of fuel, for example diesel, petrol or ethanol. Various types of a particular kind of fuel can also be used, such as different types of diesel, with a varying content of biodiesel. Various blends of fuels, such as diesel mixed with FAME (Fatty Acid Methyl Ester) can also be used in combustion engines. The various kinds, various types and various blends of fuels can all be viewed as different grades or qualities of fuel. Therefore, the concept of fuel quality includes the various kinds of fuel, the various types of fuel and the various blends of fuel. These different kinds, types and/or blends of fuel, are fuel qualities or grades, which have different properties affecting a large number of parameters in an engine system as well as other systems, for instance in a vehicle. A variety of fuel qualities can be replenished on different refuelling occasions, possibly making it difficult for a control system as well as the driver to know which fuel quality is in the fuel system on that occasion.

For example, different fuel qualities have different energy values, which affects parameters relating to e.g. engine output, engine torque and exhaust emission control for an engine powered by such fuel. The engine output and engine torque, in turn, affect a number of parameters relating to e.g. speed regulation, cruise control and automatic gear change in, say, a vehicle.

BRIEF DESCRIPTION OF THE INVENTION

Modern-day engine systems thus depend on a relatively large number of parameters governing the fuel quality of the fuel powering the engine system. In order for the engine system and other parameter-dependent systems to function properly, a knowledge of these parameters is required so that the engine system and/or other parameter-dependent systems can be adapted to the fuel quality. If the information about available fuel quality is substandard, the engine system will be suboptimal at best, since due to uncertainty surrounding the fuel quality, to be on the safe side, the engine's control system sets parameters which work acceptably for several different fuel qualities but do not function optimally for any one fuel quality. The uncertainty surrounding the fuel quality can also result in similar suboptimization for other parameter-dependent systems. For example, inferior information can lead to the assumption of an incorrect cetane rating for the fuel, that is an erroneous assumption about the fuel's ignitability. This can have a number of adverse consequences for the engine system and/or exhaust-gas scrubbing in the vehicle. At worst, the engine system's parameters will be set entirely incorrectly, which will produce inferior performance for the engine system and/or the exhaust-gas (or supercharging) system.

By way of example, owing to a lack of knowledge about the fuel quality currently being utilized, suboptimally set parameters will produce a deterioration in engine output. Suboptimally set parameters can also generate erroneous combustion pressure in the engine's cylinders and/or wrong injection timings for injecting fuel into the cylinders, which can result in faulty ignition and/or increased escape/emission of exhaust gases from the vehicle's exhaust gas treatment system. Often, in the case of faulty ignition, not all fuel supplied to the engine is used up. As a result, the unused fuel can pass through the engine and be conveyed to the exhaust gas treatment system. In an oxidation catalytic converter in the treatment system for instance, can start to burn if the exhaust gases contain fuel and hydrocarbons. An uncontrolled fire in components of the exhaust gas treatment system, e.g. in the oxidation catalytic converter, can damage or destroy the components. This leads to increased emissions due to worse exhaust gas scrubbing and/or may result in the component having to be replaced.

Modern vehicles can even contain an on-board diagnostics (OBD) system which, for example, reports whether certain quantities or variables in the vehicle, such as exhaust gas emission levels, are exceeding mandatory regulated threshold values. If such mandatory regulated threshold values are exceeded, the driver may be forced to search for a garage or workshop to have the fault corrected. Wrongly set parameters can cause such infractions and can therefore result in the vehicle malfunctioning or breaking down.

The quality of a fuel currently supplying the engine system needs to be determined in order to optimize the engine system to match that fuel quality, thus enabling better performance, lower fuel consumption and reduced emissions of harmful and/or environmentally hazardous exhaust gases, for example, to be obtained.

SUMMARY OF THE INVENTION

An object of the present invention is to provide a method and a system for detecting fuel quality that solves these problems, at least in part.

According to the present invention, a correction factor $k_{kW}$ is established for fuel as a quotient between an output $fo_{kW}$ required to propel the vehicle and a reference output $eng_{kW}$ which an engine in the vehicle is estimated to yield, i.e.

$$k_{kW} = \frac{fo_{kW}}{eng_{kW}}.$$

A correction factor $k_{NOx}$ for exhaust gas discharge/emissions is also determined by means of a quotient between a nitrogen oxide value measured in the vehicle $eng_{NOx}$ and a reference value for nitrogen oxides $ECU_{NOx}$, i.e.

$$k_{NOx} = \frac{eng_{NOx}}{ECU_{NOx}}.$$

The fuel quality of the fuel supplied to the engine is then determined on the basis of a relationship between the correction factor $k_{kW}$ for fuel and the correction factor $k_{NOx}$ for exhaust gas emissions.

According to one embodiment, the relationship between the correction factor $k_{kW}$ for fuel and the correction factor $k_{NOx}$ for exhaust gas emissions can be made up of a quotient between the correction factor $k_{kW}$ for fuel and the correction factor $k_{NOx}$ for exhaust gas emissions, where the quotient constitutes a correction factor $k_{quality}$ for quality;

$$k_{quality} = \frac{k_{kW}}{k_{NOx}}.$$

Values for this correction factor $k_{quality}$ for quality can then be compared with predetermined values for various fuel qualities, such as different fuels and different fuel blends, allowing the fuel quality to be determined simply and reliably.

The present invention makes a very slight contribution to the complexity of the vehicle and is cost-effective to implement in the vehicle, as well as being cheap to run.

Since the engine system, exhaust gas treatment system and also other systems and control systems in the vehicle are fed correct information about the fuel quality being used by the present invention, the engine system and/or other parameter-dependent systems can be optimized with regard to the fuel quality of the fuel being supplied to the engine system. This system optimization can yield a higher engine output, higher engine torque, lower fuel consumption, an enhanced driving experience, fewer breakdowns and reduced emissions of harmful and/or environmentally hazardous exhaust gases, for example.

According to one embodiment a reliability check is also provided by detecting fuel quality according to the present invention, further enabling the vehicle's control system to refine its control of the systems, since the reliability of the invention's results can be factored into the calculations.

BRIEF LIST OF FIGURES

Figure 2:
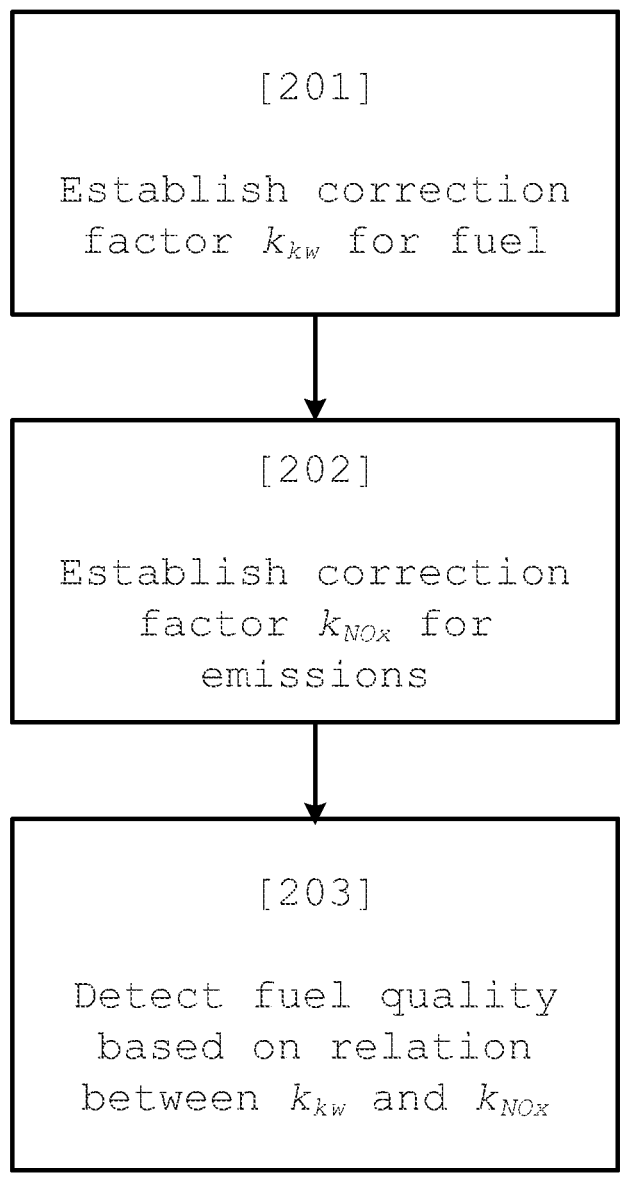
Figure 3:
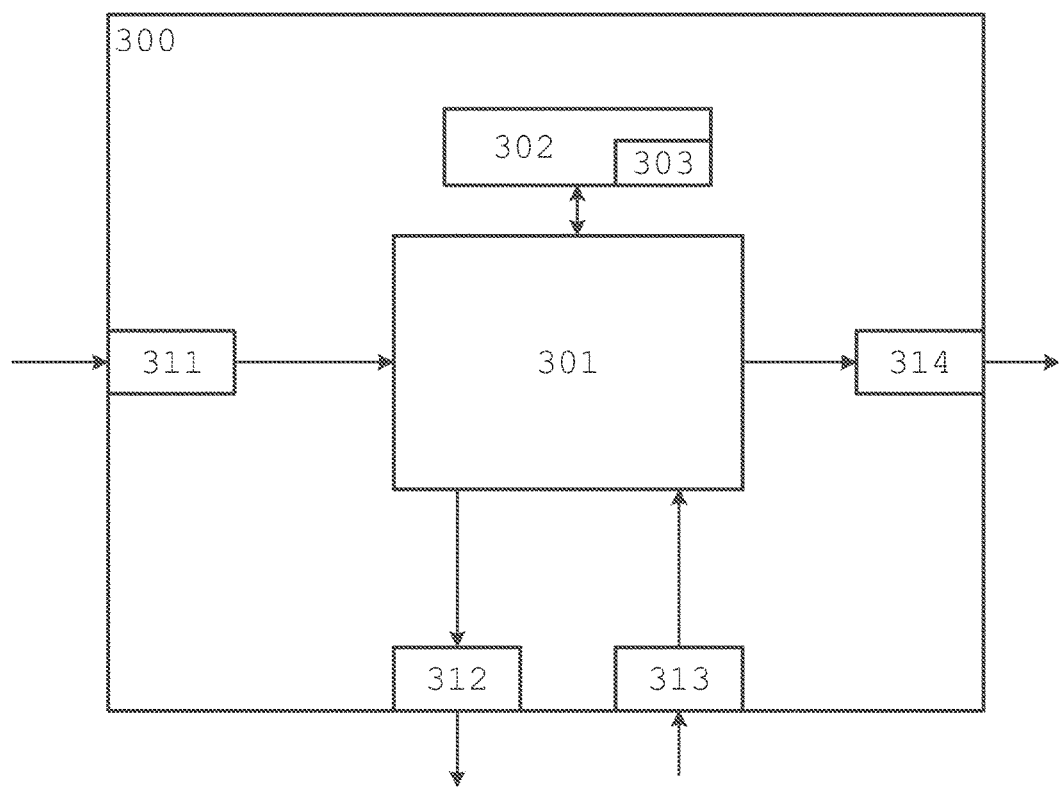

The invention will be further explained below with the aid of the drawings attached, in which similar reference designations are used for similar parts and in which:

FIG. 1 schematically shows a vehicle example in which the present invention can be implemented, FIG. 2 shows a flowchart for the method according to the present invention, and FIG. 3 shows a control unit according to the present invention.

DESCRIPTION OF PREFERRED EMBODIMENTS

In this specification, the present invention is exemplified and described chiefly for a vehicle. An expert, however, will realize that the invention can be implemented and exploited in essentially all units having an engine system or other systems affected by parameters related to fuel quality, such as water or airborne craft.

FIG. 1 schematically shows a specimen vehicle 100 which can include the present invention. The vehicle 100, which can be a passenger car, a lorry, a bus or some other vehicle, includes a power train that transmits power to drive wheels 110,111 in the vehicle 100. The power train includes a combustion engine 101 connected in customary fashion via an output shaft 102 on the combustion engine 101 to a gearbox 103 via a clutch 106. The vehicle's power train may also be of a different type, of course, such as a type with conventional automatic transmission, a type with a hybrid power train etc.

The combustion engine is powered by fuel supplied by a fuel system 120 containing, among other things, one or more fuel tanks and devices 121 that transport the fuel from the fuel tanks to the engine 101. These devices 121 are shown in highly schematic form here but can include, for example, a variety of pipes for transporting the fuel within the vehicle, one or more pumps, which can be divided into low or high-pressure circuits, filters, couplings and other devices for transporting fuel. The combustion engine 101 and/or fuel system 120 is controlled by the vehicle's control system via a control unit 140, as illustrated schematically in FIG. 1.

An output shaft 107 emanating from the gearbox 103 drives the drive wheels 110,111 via a final gear 108 such as a customary differential and drive shafts 104,105 connected with said final gear 108.

Exhaust gases from the engine 101 resulting from this combustion of fuel are scrubbed by an exhaust gas treatment system 130 before being emitted from the vehicle. The exhaust gas treatment system 130, illustrated here in highly schematic form, can include one or more components, e.g. one or more of particle filters, oxidation catalytic converters, reduction catalytic converters. Cleaning of the exhaust gases is controlled by a control unit 140 that controls e.g. dosage of reducing agent, which may contain, or be converted to, ammonia, for instance urea.

The control unit 140 according to the present invention also includes a first 141 and a second 142 determination unit and a detection unit 143, and is connected at least to the engine 101 and to the exhaust gas treatment system 130. The first 141 and second 142 determination units and the detection unit 143 are described in more detail below. The control unit 140 can be included in, and/or can exchange information and/or functions with, an engine management system (EMS) circuit in the vehicle.

FIG. 2 shows a flow chart for the method according to the present invention. By utilizing a first determination unit 401 described below, for example, a first stage 201 of the method determines a correction factor $k_{kW}$ for fuel as a quotient, where an output $fo_{kW}$ required to propel the vehicle 100 comprises the numerator and a reference output $eng_{kW}$ which an engine in the vehicle 100 is estimated to yield comprises the denominator. The correction factor $k_{kW}$ for fuel is thus established according to $$k_{kW} = \frac{fo_{kW}}{eng_{kW}}.$$

A second stage 202 of the method determines, for example by utilizing a second determination unit 142 described below, a correction factor $k_{NOx}$ for exhaust gas emissions as a quotient in which a value for nitrogen oxides $eng_{NOx}$ measured in the vehicle 100 comprises the numerator and a reference value for nitrogen oxides $ECU_{NOx}$, comprises the denominator. The correction factor $k_{NOx}$ for exhaust gas emissions is thus determined according to $$k_{NOx} = \frac{eng_{NOx}}{ECU_{NOx}}.$$

By utilizing a detection unit 143 described below, for example, a third stage 203 of the method detects the fuel quality of the fuel supplied to the engine 101 by a fuel system 120 in the vehicle. Here detection of the fuel quality is based on a relation between the correction factor $k_{kW}$ for fuel and the correction factor $k_{NOx}$ for exhaust gas emissions.

Using the method according to the present invention provides a reliable yet very robust and simple determination of the fuel quality available.

Determination of the fuel quality according to the present invention therefore requires no special sensor, as a result of which the complexity added by this solution is very limited. The present invention is therefore cost-effective to implement in the vehicle, as well as being cheap to run since maintenance of an extra sensor can be avoided.

Since the engine system and other fuel quality-dependent systems obtain correct information about the fuel quality being used through the present invention, the engine system and/or other fuel quality-dependent systems can be optimized with regard to the fuel quality of the fuel being supplied to the engine system, resulting for example in higher engine output, higher engine torque, lower fuel consumption and reduced emissions of harmful and/or environmentally hazardous exhaust gases. The information about the available fuel quality can thus be used to set a large number of parameters affecting the performance of the engine systems and/or exhaust gas treatment systems. If these parameters are correctly set, the obtainable driver's experience can also be made essentially similar for different fuel qualities.

As described above, the output $fo_{kW}$ required to propel the vehicle 100 is exploited by ascertaining the correction factor $k_{kW}$ for fuel;

$$k_{kW} = \frac{fo_{kW}}{eng_{kW}}.$$

According to one embodiment of the present invention this output $fo_{kW}$ is determined based on a driving resistance $F_{drivingres}$ acting on the vehicle and on a vehicular speed v maintained by the vehicle. Here the driving resistance $F_{drivingres}$ for the vehicle is equivalent to the external forces that have to be overcome in order for the vehicle to at least be able to keep up a constant speed, i.e. be able to maintain constant speed or accelerate. The output $fo_{kW}$ is calculated as a product of two vectors:

$$\overline{fo_{kW}} = \overline{fo_{mass}} * \overline{F_{drivingres}} \quad (equ. 1)$$

where $\overline{F_{drivingres}}$ is a vector for the driving resistance; and $$\overline{fo_{mass}} = m*\{-g*\sin(\alpha), -g*\cos(\alpha)\} \quad (equ. 2)$$

where
m is a total vehicle weight;
g is the gravitational constant; and
α is an incline or gradient in point.

Driving resistance $F_{drivingres}$ can be calculated based on at least a weight m for the vehicle, a rolling friction force $F_{roll}$ acting on the vehicle and an air resistance (drag force) $F_{air}$ acting on the vehicle.

The driving resistance $F_{drivingres}$ is the sum of rolling, air, and gradient resistances and can be written as:

$$F_{drivingres} = F_{air} + m \cdot g \cdot \sin \alpha + F_{roll} \quad (equ. 3)$$

where
m is a total vehicle weight;
g is the gravitational constant;
$F_{roll} = m \cdot g \cdot C_r$, where $C_r$ is a rolling friction coefficient;
$F_{air} = C_{air} \cdot v^2$ is the air resistance, where $C_{air}$ is the air resistance parameter and v is the vehicular speed; and
α is a gradient in point.

The driving resistance $F_{drivingres}$ can also be calculated in some other way, as any expert will appreciate, including being calculated on the air resistance $F_{air}$, air humidity, chassis dynamics, front area of the vehicle and rolling resistance $F_{roll}$. These computational methods are not detailed as they will be familiar to any expert in the field.

According to one embodiment the current gradient α can be obtained in a number of different ways. The gradient α, for example, can be determined from cartographic data, taken for example from digital maps containing topographical information combined with positioning information, such as global positioning system (GPS) information. By exploiting the positioning information, the vehicle's position in relation to the cartographic data can be established so that the gradient α can be extracted from the cartographic data, allowing highly precise and dependable ascertainment of the gradient α to be generated according to the embodiment.

A number of the cruise-control systems currently available use cartographic data and positioning information to maintain speed. Such systems can then provide the system for the present invention with the gradient α and/or cartographic data and positioning information, adding little complexity to determine the gradient α.

The gradient α can also be determined from radar information, camera information, information from another vehicle, from gradient information previously stored in the vehicle or information received from traffic systems related to said section of road. In systems exploiting the exchange of information between vehicles, a gradient α estimated by a vehicle can be fed to other vehicles, either directly or via an intermediary unit such as a database or similar.

The vehicle's weight m can be determined in a number of ways familiar to an expert in the field, for example by utilizing information from an air suspension system in the vehicle, by utilizing vehicle acceleration and/or by utilizing an accelerometer.

The rolling friction coefficient $C_r$, for example, can be determined by means of a coast-down test without providing fuel at a certain gradient, analyzing the vehicle's change in speed.

The air resistance parameter $C_{air}$ can be determined by making use of predetermined values for the parameter for the vehicle type/cab type.

According to one embodiment of the present invention the reference output $eng_{kW}$ used to establish the correction factor $k_{kW}$ for fuel;

$$k_{kW} = \frac{fo_{kW}}{eng_{kW}};$$

is related to an engine output $P_{eng}$ calculated to be yielded by the engine 101 in the vehicle 100.

The engine output $P_{eng}$ can be determined on the basis of a speed ω for the engine 101 and on the efficiency of a quantity of fuel for the fuel. For example, the engine output $P_{eng}$ can be computed as a product of a measured speed ω, a measured quantity of fuel consumed $M_{fuel}$ and an efficiency $\eta_{eng}$ for the engine 101.

The reference output $eng_{kW}$ can be determined as a product of a quantity of fuel $M_{fuel}$ consumed, an energy content $E_{fuel}$ in that fuel and an efficiency $\eta_{eng}$ for the engine 101.

According to one embodiment of the present invention the value measured for nitrogen oxides $eng_{NOx}$, which is used to determine the correction factor $k_{NOx}$ for exhaust gas emissions;

$$k_{NOx} = \frac{eng_{NOx}}{ECU_{NOx}};$$

is determined on the basis of measuring at least one nitrogen oxide sensitive sensor sited adjacent to an exhaust gas treatment system 130 in the vehicle 100. The sensor is suitably positioned so as to come into contact with the exhaust gases passing through and being cleaned by the exhaust gas treatment system 130, for example in conjunction with a reduction catalytic converter or at some other suitable position in the exhaust gas system. Many of today's exhaust gas treatment systems are already equipped with one or more sensors to measure the quantity of nitrogen oxides in the exhaust gases. Signals from such sensors can be used as measurement values according to the embodiment, allowing the embodiment to be implemented, adding very little complexity for the vehicle.

The value measured for nitrogen oxides $eng_{NOx}$ can also be determined on the basis of a standardized mass flow $\Phi_{NOx\_mass\_norm}$ of nitrogen oxides through the exhaust gas treatment system 130 and a gas flow $\Phi_{gas}$ through the engine 101 in the vehicle 100. The mass flow $\Phi_{NOx\_mass\_norm}$ of nitrogen oxides can be determined with the help of common gas laws based on pressure and temperature measurements for the exhaust gases as well as sensor measurements of the proportion of nitrogen oxides $NO_x$ in the exhaust gases. By the same token, the gas flow $\Phi_{gas}$ through the engine can be determined as the mass flow $\Phi_{NOx\_mass\_norm}$.

According to the various embodiments of the present invention relating to nitrogen oxides $NO_x$, therefore, use is made of the knowledge that different fuels/fuel blends yield different levels of nitrogen oxides $NO_x$ in the exhaust gases. For example, it can be mentioned that diesel with an admixture of FAME (Fatty Acid Methyl Ester) burns faster and therefore yields higher levels of nitrogen oxides $NO_x$ than does pure diesel, i.e. a fuel with 100% diesel.

According to one embodiment the nitrogen oxide levels are measured at different operating points for the engine 101 for different fuels and for different fuel blends. These levels are then used to detect the fuel quality according to the present invention.

According to one embodiment of the present invention the reference value for the nitrogen oxides is $ECU_{NOx}$, which is exploited in determining the correction factor $k_{NOx}$ for exhaust gas emissions;

$$k_{NOx} = \frac{eng_{NOx}}{ECU_{NOx}};$$

a predetermined value for a predetermined fuel. This value has been determined on the basis of the respective fuel's combustion properties, the exhaust gases being measured upstream of the exhaust gas treatment system. If the vehicle 100 is powered primarily by diesel, for example, the predetermined fuel will be diesel, and the reference value for the nitrogen oxides $ECU_{NOx}$ will have a predetermined value for diesel, which is used to establish the correction factor $k_{NOx}$ for the exhaust gas discharge/emissions.

By the same token, the reference value for the nitrogen oxides $ECU_{NOx}$ has a predetermined value for ethanol if the vehicle is powered primarily by ethanol, using the ethanol reference value $ECU_{NOx}$ to establish the correction factor $k_{NOx}$ for the exhaust gas emissions.

By the same token, for vehicles powered primarily by other fuels/fuel blends, the reference value for the nitrogen oxides $ECU_{NOx}$ is used for this fuel/fuel mixture which is mainly in use.

As mentioned above, the quality of fuel used in the vehicle is detected/established from a relation between the correction factor $k_{kW}$ for fuel and the correction factor $k_{NOx}$ for exhaust gas emissions. This relation, according to one embodiment of the invention, is equivalent to a correction factor $k_{quality}$ for quality, which is calculated as a quotient between the correction factor $k_{kW}$ for fuel and the correction factor $k_{NOx}$ for exhaust gas emissions;

$$k_{quality} = \frac{k_{kW}}{k_{NOx}}.$$

In other words, the relation between the correction factor $k_{kW}$ for fuel and the correction factor $k_{NOx}$ for exhaust gas emissions is equivalent to a quotient where the correction factor $k_{kW}$ for fuel comprises the numerator and the correction factor $k_{NOx}$ for exhaust gas emissions comprises the denominator;

$$k_{quality} = \frac{k_{kW}}{k_{NOx}}.$$

This correction factor $k_{quality}$ for quality can then be compared with one or more predetermined intervals corresponding to a known fuel quality, enabling fuel quality detection to be ascertained. The fuel quality, therefore, is established as the quality within whose corresponding interval the value for the correction factor $k_{quality}$ lies. These predetermined intervals can be designed in a number of ways, and stored in the control unit in which the invention is implemented in a number of ways, e.g. in the form of tables, folders, reference lines or the like, and can consist of absolute numbers, percentages, quotients or other absolute or relative quantities.

The idea is that the quality correction factor $k_{quality}$ should first be determined, and this value should then be compared in some appropriate fashion with equivalent known values for different fuels and/or fuel blends, enabling the fuel or fuel mixture supplied to the engine 101 by the fuel system 120 in the vehicle to be established/detected. Once this fuel or fuel mixture has been ascertained, one or more parameters for the engine system 101, and the exhaust gas treatment system 130, and for other systems in the vehicle which depend on the fuel or fuel mixture used can be updated in order to be optimized in line with the fuel quality established.

Table 1 below describes approximate values corresponding to the correction factor $k_{NOx}$ for exhaust gas emissions, the correction factor $k_{kW}$ for fuel and the correction factor for quality $$k_{quality} = \frac{k_{kW}}{k_{NOx}}$$

for a couple of different fuel qualities, such as various fuels and fuel blends, provided that the vehicle's primary fuel is diesel, because the reference value for nitrogen oxides $ECU_{NOx}$ and the reference output $eng_{kW}$ relate to diesel. Equivalent tables can be compiled for other primary fuels and other fuels and/or fuel blends, as any expert will understand.

Thus, having determined the quality correction factor $k_{quality}$ according to the present invention, this value is then compared with the values in the table for different fuel qualities, and the table value closest in some sense to the value determined for the quality correction factor $k_{quality}$ is established as being equivalent to the fuel quality currently being used in the vehicle. This provides a robust and reliable determination of the fuel quality in the vehicle.

TABLE 1

| $k_{kW}$ | $k_{NOx}$ | $k_{quality}$ | Fuel quality |
|---|---|---|---|
| 1 | 1 | 1 | 100% diesel |
| 0.7 | 0.4 | 1.7 | 100% ethanol |
| 0.9 | 1.3 | 0.7 | 100% FAME |
| 0.8 | 1.16 | 0.8 | 50% diesel and 50% FAME |

According to one embodiment of the present invention a reliability check is carried out on the detection of the fuel quality, further ensuring that the on-board parameter values updated on the basis of said detection receive correct readings. The reliability check can be performed by an analysis of any change in the correction factor $k_{kW}$ for fuel and any change in the correction factor $k_{NOx}$ for exhaust gas emissions.

If the change to the correction factor $k_{kW}$ for fuel and the change to the correction factor $k_{NOx}$ for exhaust gas emissions behave essentially uniformly in some sense, fuel quality detection is deemed to be reliable. This essentially uniform behaviour may consist, for example, of the values for both the correction factor $k_{kW}$ for fuel and the correction factor $k_{NOx}$ for exhaust gas emissions increasing essentially simultaneously, for instance, after refuelling, and/or the values for both the correction factor $k_{kW}$ for fuel and the correction factor $k_{NOx}$ for exhaust gas emissions decreasing essentially simultaneously.

Similarly, fuel quality detection is deemed to be unreliable if the changes to the correction factor $k_{kW}$ for fuel and the correction factor $k_{NOx}$ for exhaust gas emissions are not uniform, which is to say they are physically incompatible. This non-uniform behaviour may arise, for example, if one of the values for the correction factor $k_{kW}$ for fuel and the correction factor $k_{NOx}$ for exhaust gas emissions increases while the other decreases essentially at the same time, following refuelling for example.

The fuel quality of the fuel in a vehicle, say, may typically change when refilling the vehicle, which is to say when the fuel system 120, which contains one or more fuel tanks, is replenished with fresh fuel. According to one embodiment, therefore, fuel quality detection is performed when the vehicle has been refilled with fuel.

Such refuelling can be identified by measuring/estimating the fuel level in one or more of the vehicle's fuel tanks, refuelling being gauged to have taken place when a fuel level in a fuel tank has increased at least 20% since a previous level measurement. Other ways of identifying refuelling in progress, for example an indication that a tank lid is being opened, can also be used to identify a refuelling event, as any expert will realize.

According to one embodiment of the present invention, detection of the fuel quality is performed under essentially stationary conditions for the vehicle, where such stationary conditions may involve, say, a way of driving that produces essentially constant driving resistance and/or an essentially constant power drain on the engine.

The vehicle's essentially stationary conditions can be tantamount to the engine 101 having had a speed ω within an interval equal to ±10 r.p.m., and a load L within an interval equal to ±50 Nm during a time interval $T_1$-$T_2$ min., where this time interval may be 2-3 minutes long, for example.

These essentially stationary conditions can often be achieved in transit on a main road and/or motorway. So if normal main road driving or normal motorway driving—during which these normal drives may involve, for example, the essentially constant driving resistance described above and/or a power drain and/or speed and/or loads—has gone on for a predetermined time interval, $T_1$-$T_2$ min., for example 2-3 minutes, then according to one embodiment such essentially stationary conditions are deemed to exist, in which case fuel quality detection can be performed.

The expert will realize, moreover, that a method for detecting fuel quality according to the present invention can be implemented in a computer program, which when executed in a computer causes the computer to execute the method. The computer program usually forms part of a computer software product 303, in which the software product includes a suitable digital storage medium on which the computer program is stored. Said computer-readable medium consists of a suitable memory, such as: ROM (Read-Only Memory), PROM (Programmable Read-Only Memory), EPROM (Erasable PROM), Flash memory, EEPROM (Electrically Erasable PROM), a hard-disk unit etc.

FIG. 3 schematically shows a control unit 300. The control unit 300 contains a calculation unit 301, which may essentially be made up of some suitable type of processor or microcomputer, e.g. a circuit for digital signal processing (Digital Signal Processor, DSP), or a circuit with a specific predetermined function (Application Specific Integrated Circuit, ASIC). The calculation unit 301 is connected to a memory unit 302 housed in the control unit 300, providing the calculation unit 301 with e.g. the stored program code and/or the stored data which the calculation unit 301 needs in order to be able to perform calculations. The calculation unit 301 is also configured to store the partial or final result of calculations in the memory unit 302.

Furthermore, the control unit 300 is fitted with devices 311, 312, 313, 314 for receiving and/or transmitting input or output signals, respectively. These input or output signals, as appropriate, can contain wave forms, pulses or other attributes which can be detected as information by the input signal receiving devices 311, 313 and transformed into signals that can be processed by the calculation unit 301. These signals are then fed to the calculation unit 301. The devices 312, 314 for transmitting output signals are configured to transform the computational result from the calculation unit 301 into output signals for transfer to other parts of the vehicle's control system and/or the component(s) for which the signals are intended.

Every single connection to the devices for receiving and/or transmitting input or output signals, respectively, can be comprised of one or more of a cable, a data bus such as a CAN (Controller Area Network) bus, a MOST (Media Orientated Systems Transport) bus or some other bus configuration, or else a wireless connection.

An expert will realize that the above-mentioned computer can be comprised of the calculation unit 301 and that the above-mentioned memory can be comprised of the memory unit 302. An expert will also realize that the above-mentioned control unit 140 can be comprised of a control unit equivalent to the control unit 300 described with reference to FIG. 3.

In general, the control systems in modern vehicles consist of a communications bus system comprising one or more communications buses for interconnecting a number of electronic control units (ECUs) or controllers, and various components located on the vehicle. A control system of this sort can include a large number of control units, and responsibility for a specific function can be divided between more than one control unit. Vehicles of the type shown, therefore, often include considerably more control units than are shown in FIG. 3, a fact well-known to the expert in this field of engineering.

In the embodiment illustrated the present invention has been implemented in the control unit 300. However, the invention can also be partly or fully implemented in one or more other control units already in existence on the vehicle or in some dedicated control unit for the present invention.

According to one aspect of the present invention the system provided is configured to detect a fuel quality in a vehicle 100. The system according to the invention contains a first determination unit configured to determine a correction factor $k_{kW}$ for fuel as a quotient between an output $fo_{kW}$ required to propel vehicles 100 and a reference output $eng_{kW}$ which an engine 101 in the vehicle 100 is estimated to yield;

$$k_{kW} = \frac{fo_{kW}}{eng_{kW}}.$$

The system also includes a second determination unit 142 configured to determine a correction factor $k_{NOx}$ for exhaust gas emissions as a quotient between an in-vehicle 100 value measured for nitrogen oxides $eng_{NOx}$ and a reference value for nitrogen oxides $ECU_{NOx}$;

$$k_{NOx} = \frac{eng_{NOx}}{ECU_{NOx}}.$$

The system also includes a detection unit 143 configured to detect the fuel quality, such as which fuel or fuel blend the fuel system 120 supplies to the engine 101, based on a relation between the correction factor $k_{kW}$ for fuel and the correction factor $k_{NOx}$ for exhaust gas emissions.

According to one embodiment this relation between the correction factor $k_{kW}$ for fuel and the correction factor $k_{NOx}$ for exhaust gas emissions represents a quotient equivalent to a correction factor $k_{quality}$ for quality;

$$k_{quality} = \frac{k_{kW}}{k_{NOx}}.$$

The system according to the present invention can be configured to perform all method embodiments described above and in the patent claim, the system for each respective embodiment having the advantages described above for each embodiment.

An expert will also realize that the above system can be modified according to the various embodiments of the method according to the invention. In addition the invention relates to a motorized vehicle 100, for example a lorry or a bus, containing at least one system for detecting fuel quality according to the present invention.

The present invention is not confined to the embodiments of the invention described above but relates to and includes all embodiments within the scope of protection of the independent claims attached.

The invention claimed is:

1. A method of operating a vehicle having a system with a parameter that can be optimized based on fuel quality, comprising:
   determining a correction factor $k_{kW}$ for fuel as a quotient between an output $fo_{kW}$ required to propel said vehicle and a reference output $eng_{kW}$ which an engine in said vehicle is estimated to yield;

$$k_{kW} = \frac{fo_{kW}}{eng_{kW}};$$

determining a correction factor $k_{NOx}$ for exhaust gas emissions as a quotient between a value measured in said vehicle for nitrogen oxides $eng_{NOx}$ and a reference value for nitrogen oxides $ECU_{NOx}$;

$$k_{NOx} = \frac{eng_{NOx}}{ECU_{NOx}};$$

detecting said fuel quality based on a relation between said correction factor $k_{kW}$ for fuel and said correction factor $k_{NOx}$ for exhaust gas emissions,
   updating said parameter of said system of said vehicle based on said detected fuel quality, and
   operating said system of said vehicle based on said updated parameter, wherein said system of said vehicle is a system with a parameter that can be optimized based on fuel quality,
   wherein said system is the vehicle's engine system or the vehicle's exhaust gas treatment system.

2. A method according to claim 1, further comprising determining said output $fo_{kW}$ required to propel said vehicle based on a driving resistance $F_{drivingres}$ acting on said vehicle and on a vehicular speed v of said vehicle.

3. A method according to claim 2, wherein said driving resistance $F_{drivingres}$ comprises external forces to be overcome for said vehicle to maintain a constant speed or to accelerate.

4. A method according to claim 3, further comprising calculating said driving resistance $F_{drivingres}$ based on at least a weight m for said vehicle, a rolling friction force $F_{roll}$ acting on said vehicle and an air resistance force $F_{air}$ acting on said vehicle.

5. A method according to claim 1, wherein said reference output $eng_{kW}$ is related to an engine output $P_{eng}$ calculated to be yielded by an engine in said vehicle.

6. A method according to claim 5, wherein said engine output $P_{eng}$ is determined based on a speed ω for said engine and on efficiency of a quantity of a selected fuel for said fuel.

7. A method according to claim 1, further comprising said reference output $eng_{kW}$ based on a quantity $M_{fuel}$ of fuel consumed, an energy content $E_{fuel}$ in said fuel and an efficiency $n_{eng}$ for said engine.

8. A method according to claim 7, further comprising determining said measured value for nitrogen oxides $eng_{NOx}$ based on a standardized mass flow $\Phi_{NOx\_mass\_norm}$ of nitrogen oxides through said exhaust gas treatment system and a gas flow $\Phi_{gas}$ through said engine in said vehicle.

9. A method according to claim 1, further comprising determining an estimated value for nitrogen oxides $eng_{NOx}$ based on a measurement by at least one nitrogen oxide-sensitive sensor placed near an exhaust gas treatment system in said vehicle.

10. A method according to claim 1, wherein said reference value for nitrogen oxides $ECU_{NOx}$ represents a predetermined value for a predetermined fuel.

11. A method according to claim 10, wherein said predetermined fuel is comprised of diesel.

12. A method according to claim 1, further comprising said detecting of said fuel quality is based on a quality correction factor $k_{quality}$, and calculating said quality correction factor as a quotient between said correction factor $k_{kW}$ for fuel and said correction factor $k_{NOx}$ for exhaust gas emissions;

$$k_{quality} = \frac{k_{kW}}{k_{NOx}}.$$

13. A method according to claim 12, further comprising determining said detecting of said fuel quality by comparing a value for said quality correction factor $k_{quality}$ with at least a predetermined interval corresponding to a known fuel quality.

14. A method according to claim 12, wherein, if a predetermined fuel, to which said reference value for nitrogen oxides $ECU_{NOx}$ and said reference output $eng_{kW}$ relate, is comprised of diesel, said correction factor $k_{quality}$ has a value equal to one of the group:

$k_{quality} \approx 1$, which is equivalent to $k_{kW} \approx 1$ and $k_{NOx} \approx 1$, when said fuel contains 100% diesel;

$k_{quality} \approx 1.7$, which is equivalent to $k_{kW} \approx 0.7$ and $k_{NOx} \approx 0.4$, when said fuel contains 100% ethanol;

$k_{quality} \approx 0.7$, which is equivalent to $k_{kW} \approx 0.9$ and $k_{NOx} \approx 1.3$, when said fuel contains 100% FAME (Fatty Acid Methyl Ester); and $k_{quality} \approx 0.8$, which is equivalent to $k_{kW} \approx 0.98$ and $k_{NOx} \approx 1.16$, when said fuel contains 50% FAME.

15. A method according to claim 14, wherein said detecting of fuel quality is deemed reliable if said changes to said correction factor $k_{kW}$ for fuel and to said correction factor $k_{NOx}$ for exhaust gas emissions are uniform.

16. A method according to claim 14, wherein said detecting of fuel quality is deemed unreliable if said changes to said correction factor $k_{kW}$ for fuel and to said correction factor $k_{NOx}$ for exhaust gas emissions are not uniform.

17. A method according to claim 1, further comprising performing a reliability check on said detection of fuel quality by analyzing a change to said correction factor $k_{kW}$ for fuel and a change to said correction factor $k_{NOx}$ for exhaust gas emissions.

18. A method according to claim 1, further comprising said detection of fuel quality is performed after a refilling of said fuel in said vehicle.

19. A method according to claim 18, wherein said refilling of said fuel is deemed to have taken place when a fuel level in a fuel tank in said vehicle has increased at least 20% since a previous level measurement.

20. A method according to claim 1, further comprising detecting said fuel quality under essentially stationary conditions of said vehicle.

21. A method according to claim 20, wherein said essentially stationary conditions are equivalent to an engine in said vehicle having had a speed ω within an interval equal to ±10 r.p.m., and a load L within an interval equal to ±50 Nm during a time interval $T_1$-$T_2$ min.

22. A method according to claim 20, wherein said essentially stationary conditions are equivalent to normal main road and/or motorway driving having taken place during a predetermined time interval $T_1$-$T_2$ min.

23. A computer software product including a non-transitory computer-readable medium and a computer program stored on said readable medium;

said computer program comprising program code configured such that when said program code is executed in a computer, said code causes said computer to execute the method in accordance with claim 1.

* * * * *